United States Patent [19]

Mueller

[11] Patent Number: 5,403,597
[45] Date of Patent: Apr. 4, 1995

[54] LOW CONCENTRATION PHOSPHINE FUMIGATION METHOD

[76] Inventor: David K. Mueller, P.O. Box 4064, Indianapolis, Ind. 46280

[21] Appl. No.: 155,705

[22] Filed: Nov. 22, 1993

[51] Int. Cl.⁶ .................... A01N 59/26; A01N 59/04; A01M 13/00
[52] U.S. Cl. .................................. 424/601; 424/602; 424/606; 424/700; 43/125; 422/32
[58] Field of Search .............. 424/601, 700, 602, 606; 43/125; 422/32

[56] References Cited

U.S. PATENT DOCUMENTS

| | | | |
|---|---|---|---|
| 2,826,527 | 3/1958 | Huter | 424/601 |
| 4,814,154 | 3/1989 | Doernemann et al. | 423/299 |
| 4,989,363 | 2/1991 | Doernemann | 43/124 |
| 4,998,377 | 3/1991 | Tsutsumi et al. | 43/125 |
| 5,015,475 | 5/1991 | Kapp et al. | 424/405 |

OTHER PUBLICATIONS

Kashi et al., "The toxic Action of Phosphine:Role of Carbon dioxide on the Toxicity of Phosphine to Sitophilus granarius (L.) and Tribolium Confusum DuVal", J. Stored Prod. Res., vol. 11(1), 1975, pp. 9–15.

Rajendran et al., "The toxic Action of Phosphine in Combination with Some alkyl Halide Fumigants and Carbondioxide Against the eggs of Tribolium Castaneum Herbst (Coleoptera:Tenebrionidae)", J. Stored Prod. Res., vol. 25(4), 1989, pp. 225–230.

*Primary Examiner*—Allen J. Robinson
*Assistant Examiner*—John D. Pak
*Attorney, Agent, or Firm*—Locke Reynolds

[57] ABSTRACT

A method for fumigating an enclosed structure includes release of sufficient phosphine into the enclosed structure to maintain an average concentration of between about 50 ppm and 500 ppm phosphine. Concurrently, sufficient carbon dioxide is released into the enclosed structure to maintain an average concentration of between about 4% and 10% carbon dioxide, and a temperature of between about 30 degrees Celsius to about 40 degrees Celsius is maintained in the enclosed structure to enhance fumigation effectiveness.

4 Claims, 9 Drawing Sheets

LOW CONCENTRATION PHOSPHINE FUMIGATION METHOD

BACKGROUND AND SUMMARY OF THE INVENTION

The present invention relates to phosphine based fumigation methods for controlling pests. More particularly, the present invention relates to a combination of phosphine, carbon dioxide, and elevated heat disseminated through a building interior to eradicate pests.

Fumigation is a conventional method for controlling pests in buildings, storage facilities, shipholds, trucks, factories, human habitations, or other enclosable structures. Toxic fumes or vapors are released into an enclosable structure for a limited time to exterminate rodents, insects, worms, and other destructive or infectious organisms. Conventional fumigants have included highly toxic chemicals such methyl bromide, hydrogen cyanide, ethylene dibromide, ethylene oxide, sulfur dioxide, tetrachloride, and podichlorobenzene. However, because of their extreme toxicity, bioaccumulation potential, and persistence, use of many such fumigants is now banned or tightly regulated.

Because of the hazards associated with conventional fumigants, fumigators have begun widespread use of phosphine (hydrogen phosphide) as a replacement fumigant. Phosphine leaves minimal toxic residue, does not accumulate in the biological food chain, and is relatively inexpensive. Phosphine is comparatively simple to produce at the fumigation location, typically being produced by reacting moisture with a hydrolysable metal phosphide composition such as magnesium or aluminum phosphide.

However, even phosphine fumigation is not without problems. Phosphine is itself a toxic chemical requiring care in preparation and use, and can require substantial amount of time to be ventilated from large, multileveled enclosable structures such as a building, warehouse, or storage facility. In addition, even low levels of phosphine have a detectable odor that requires time to be eliminated from the building. Conventional treatment of buildings with 500 ppm or greater phosphine concentration can require from three to ten days for treatment and aeration before the building is ready for human occupancy. While this time requirement is not of great concern for granary storage bins or the like, such substantial fumigation time greatly limits the potential for fumigation of factories or other human occupied structures.

In an effort to eliminate the use of highly toxic and bioreactive vapors, an inert gas such carbon dioxide can be employed as fumigant. For example, U.S. Pat. No. 4,989,363 to Doernemann describes a process for slowly admitting carbon dioxide in the bottom of a sealed structure while venting air originally contained in the sealed structure. Carbon dioxide is maintained in the sealed structure at a high concentration of 60% to as much as 100% for long period of time (e.g. 5–80 days), suffocating any pests in the building. While effective, this procedure has been found to be time consuming and expensive for general use.

What is needed is a fumigation method that is uses minimal amounts of toxic chemicals, is easy and inexpensive to apply, and requires a limited amount of time for action. The present invention satisfies these needs by provision of a method for fumigating an enclosed structure that includes the steps of releasing sufficient phosphine into the enclosed structure to maintain an average concentration of less than 500 ppm phosphine. In preferred embodiments less than 200 ppm phosphine is utilized, and in a most preferred embodiment between about 50 ppm and 150 ppm phosphine is released. Concurrently, carbon dioxide is released into the enclosed structure to maintain an average concentration of less than 20% carbon dioxide, preferably between about 4% and 10% carbon dioxide, and a temperature of greater than about 30 degrees Celsius, preferably between about 30 degrees Celsius to about 40 degrees Celsius, is maintained in the enclosed structure to enhance fumigation effectiveness.

Alternatively, the present invention provides for release of sufficient phosphine into the enclosed structure to maintain an average concentration of less than 500 ppm phosphine, and preferably between about 50 ppm and 150 ppm phosphine, for a time not to exceed 72 hours, and preferably about 12 to about 24 hours, while simultaneously releasing sufficient carbon dioxide into the enclosed structure to maintain an average concentration of between about 4% and 10% carbon dioxide for a time not to exceed 72 hours. Another embodiment of the invention relies on the synergistic pesticidal effect of phosphine and heat, requiring release of sufficient phosphine into the enclosed structure to maintain an average concentration of less than 200 ppm, and preferably between about 50 ppm and 150 ppm phosphine, for a time not to exceed 72 hours, while raising the temperature of the enclosed structure to above about 30 degrees Celsius, and preferably to a temperature between about 30 degrees Celsius to about 40 degrees Celsius.

In preferred embodiments, hydrolysis of a metal phosphide such as magnesium phosphide is used to release phosphine. Enough phosphine is released to maintain a desired concentration for a limited time usually not exceeding about 72 hours. In a most preferred embodiment, the time is limited to between about 24 hours to about 48 hours. With such a limited required fumigation time, it is possible to fumigate over a weekend or holidays, causing minimal interruption of work in a factory or other human occupied building.

Additional objects, features, and advantages of the present invention will be apparent upon consideration of the following detailed description and accompanying drawings.

BRIEF DESCRIPTION OF THE DRAWINGS

FIGS. 1–3 are graphs indicating phosphine concentration as a function of time, with FIG. 1 illustrating phosphine concentration at Purdue Feed Mills, West Lafayette, Ind., with a filled square indicating measurements taken on a lower floor and a square outline indicating measurements taken on an upper floor; FIG. 2 illustrating phosphine concentration at Hawaiian Flour Mills, Honolulu, Hi., with a filled square indicating measurements taken on a lower floor and a square outline indicating measurements taken on an upper floor; and FIG. 3 illustrating phosphine concentration at Star of the West, Frankenmuth, Mich.;

FIGS. 4–6 are graphs indicating carbon dioxide concentration as a function of time, with FIG. 4 illustrating carbon dioxide concentration at Purdue Feed Mills, West Lafayette, Ind.; FIG. 6 illustrating carbon dioxide concentration at Star of the West, Frankenmuth, Mich.; and FIGS. 7-9 are graphs indicating temperature as a function of time, with FIG. 7 illustrating temperature at Purdue Feed Mills, West Lafayette, Ind., with a filled square indicating measurements taken on a lower floor and a square outline indicating measurements taken on an upper floor; FIG. 8 illustrating temperature at Hawaiian Flour Mills, Honolulu, Hi.; and FIG. 9 illustrating temperature at Star of the West, Frankenmuth, Mich.

DETAILED DESCRIPTION OF THE INVENTION

Operation of the method of the present invention requires a source of phosphine (hydrogen phosphide), a source of carbon dioxide, and a mechanism for maintaining an elevated temperature in a building for an extended period of time. In preferred embodiments phosphine is created on site by hydrolysation of metal phosphides such as aluminum or magnesium phosphide. Because of its wide availability as a high pressure gas, as a pressurized liquid in canisters, or as a low temperature solid, carbon dioxide is typically transported to the fumigation site. Heating systems can include natural mechanisms such as solar heating of the building (typical in tropical or semitropical locations), or can be artificially provided by steam, natural gas, or electric heaters in colder climates.

As will be appreciated by those skilled in the art, the amount of phosphine and carbon dioxide released into the building is a calculable function of the volume of the building. Phosphine and carbon dioxide sensors may be used to adjust the amount and timing of phosphine and carbon dioxide release to maintain concentration within predetermined parameters, while thermometers or electronic thermistors can be used to monitor and control temperature within the building.

The following example compares the effectiveness of treatment in accordance with the present invention. Three mills were selected for treatment for a limited time period not to exceed about 72 hours. Phosphine concentration, carbon dioxide concentration, and temperature were periodically monitored. Effectiveness of the fumigation treatment was measured with insect assays.

EXAMPLE

Experimental fumigation tests were conducted at three mills during the summer of 1993. The first mill, Purdue Feed Mill, was a two story, 1700 cubic meter at Purdue University in West Lafayette, Ind.. The second mill was Hawaiian Flour Mills, a six story, 5100 cubic meter flour mill in Honolulu, Hi. The third mill was Star of West Mill, a six story, 8500 cubic meter flour mill in Frankenmuth, Mich.

Phosphine was obtained from hydrolisation of Degesch FUMI-CEL and Degesch FUMI-STRIP, a magnesium phosphide formulation commercially available as a solid plate. Each solid plate can generate 33 grams of phosphine (hydrogen phosphide) gas. Because of its quick phosphine generation, use of magnesium phosphide is preferred over standard aluminum phosphide formulations. A minimum concentration of 100 ppm can be achieved in seven hours at 32 degrees Celsius and 50% RH compared to eleven hours with aluminum phosphide at the same dosage rate and conditions.

Figure 1:
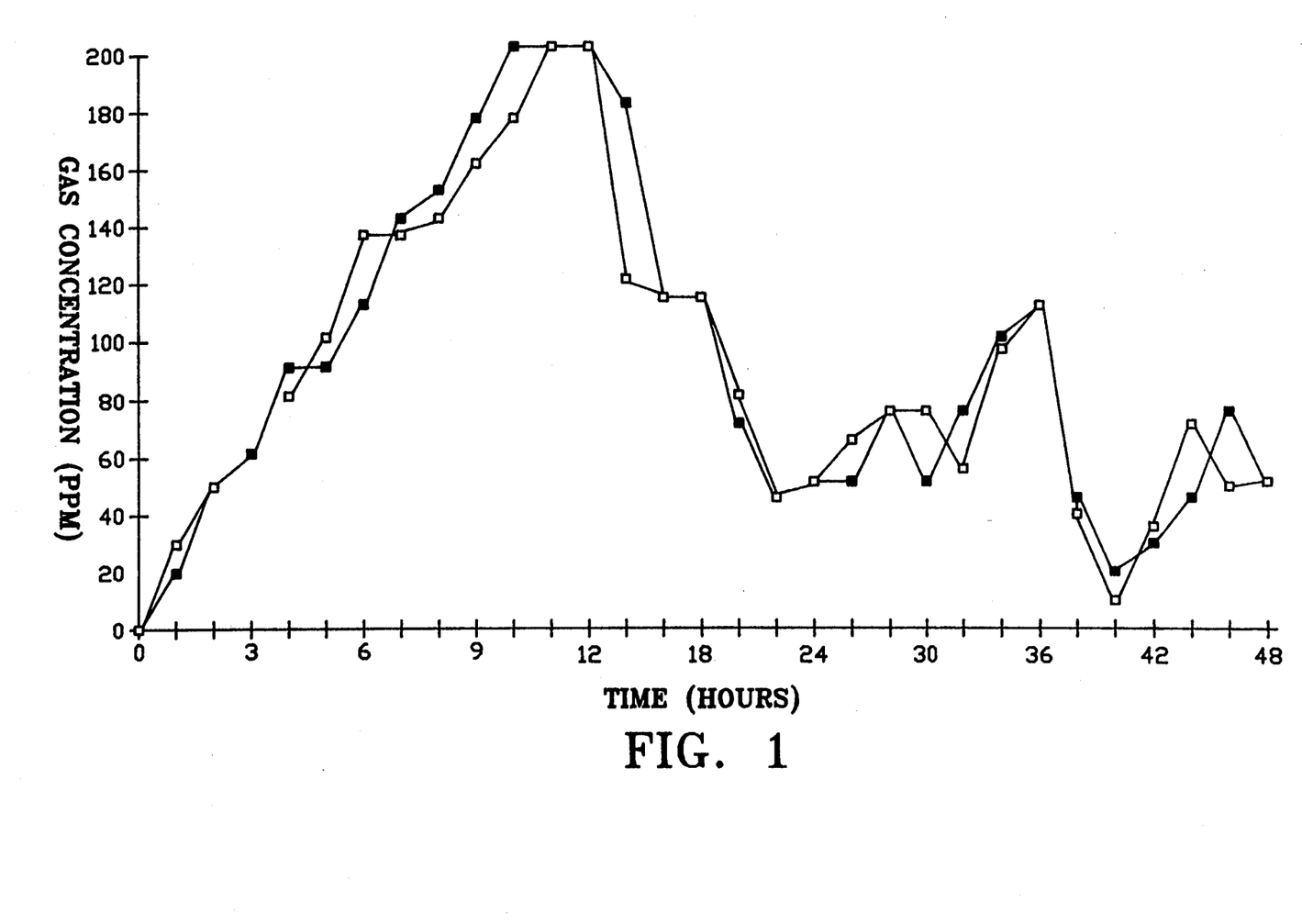
Figure 2:
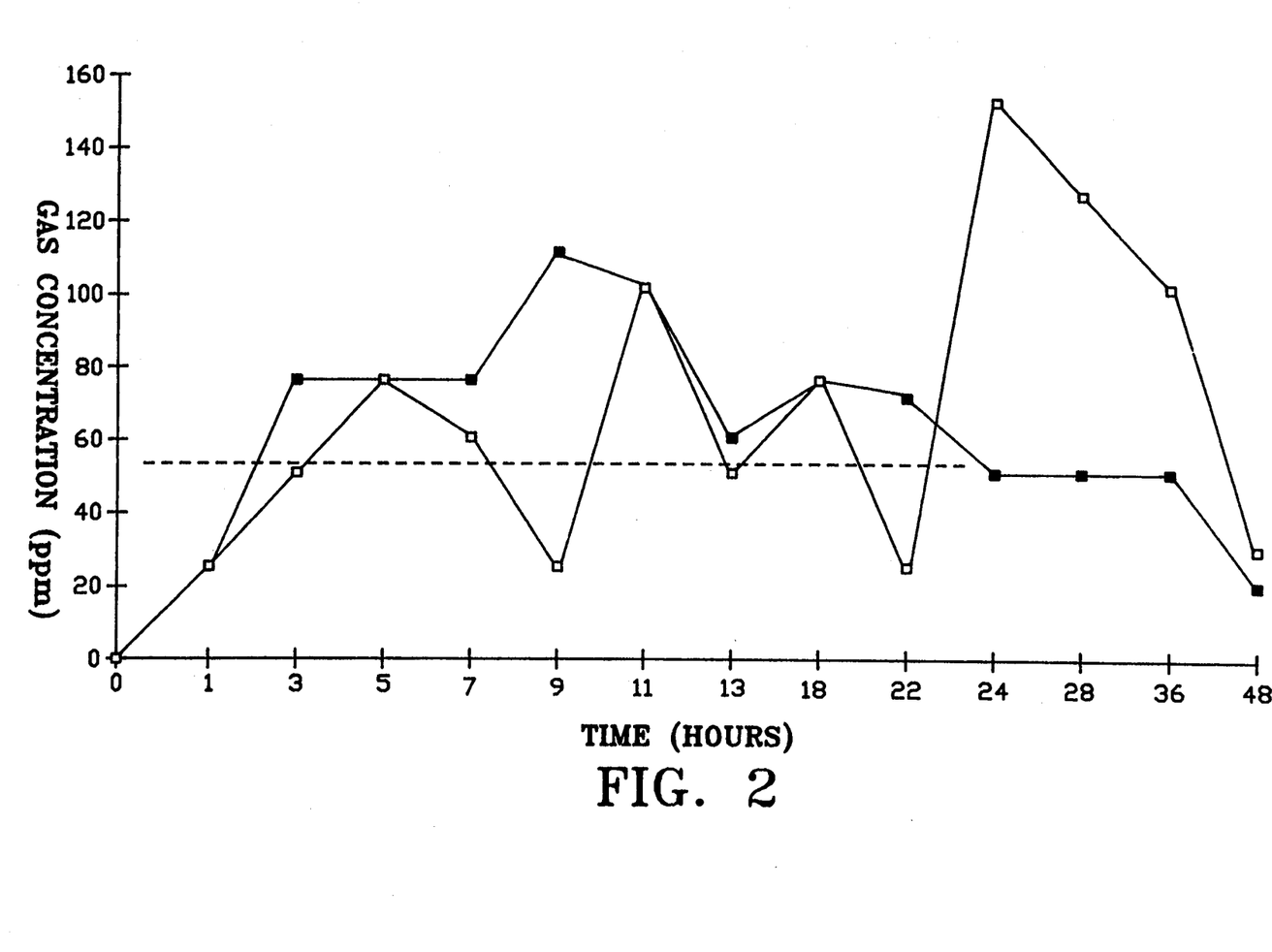
Figure 3:
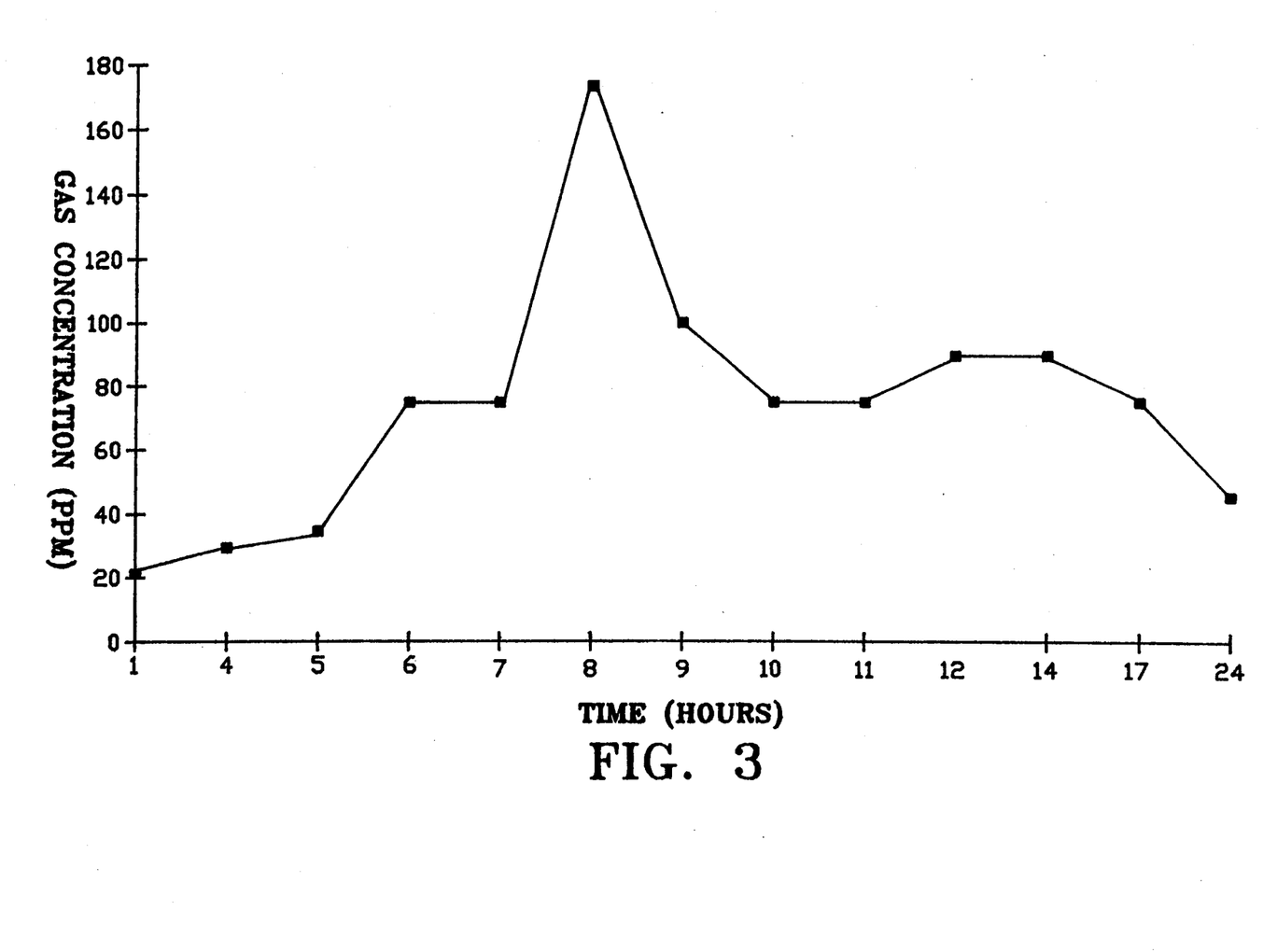

A dosage rate of about 6.7 grams per 30 cubic meters was used to treat all three mills. The theoretical maximum concentration for this dosage rate is 165 ppm. This concentration is significantly lower than a conventional fumigation with phosphine alone, which typically requires a concentration between 850 ppm and 1500 ppm. Each of the three locations showed a peak concentration of over 50% of the theoretical maximum concentration, representative of a well sealed building. FIGS. 1 through 3 respectively illustrate phosphine concentration as a function of time for the Purdue Feed Mill, the Hawaiian Flour Mill, and the Star of the West Mill.

Figure 4:
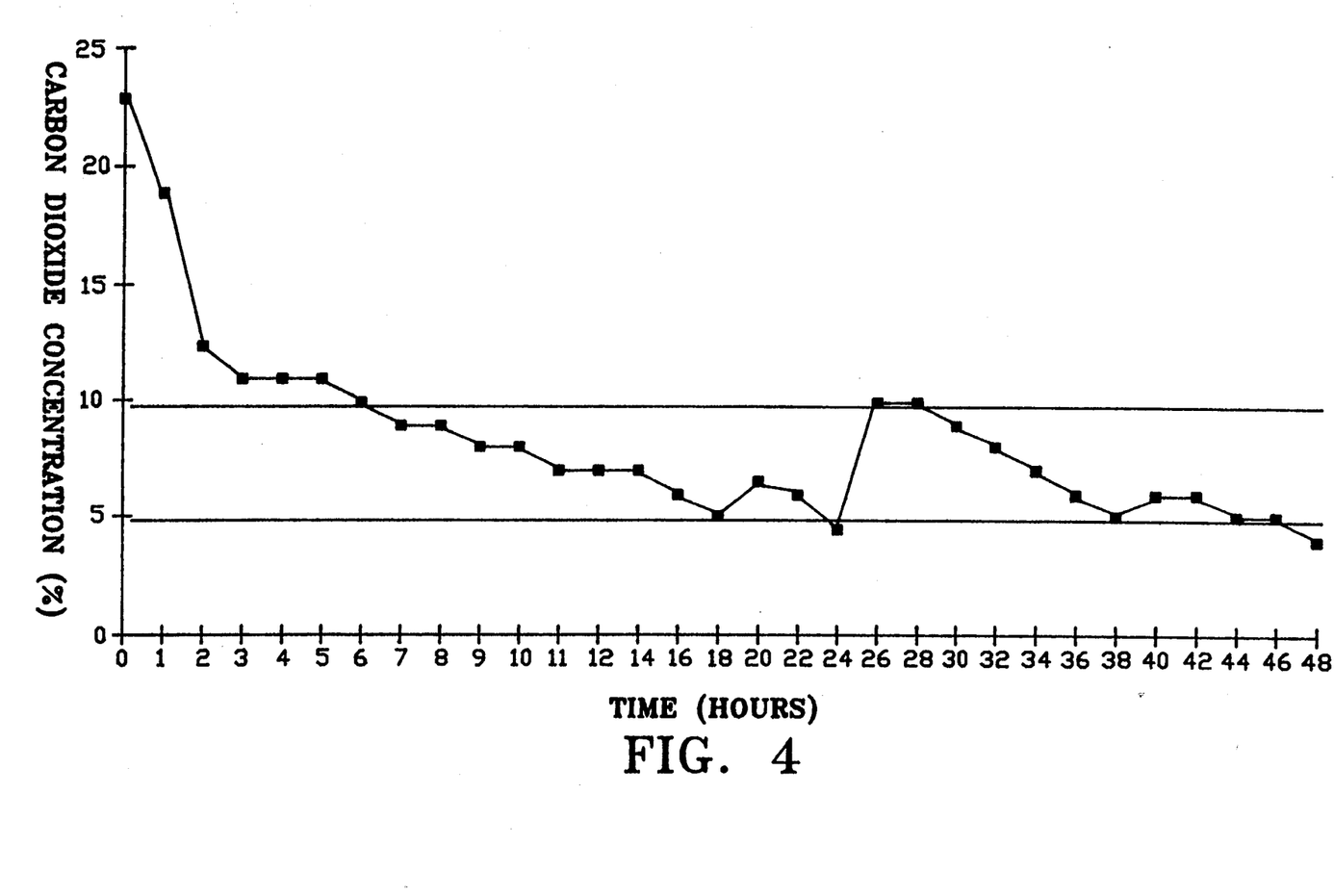
Figure 5:
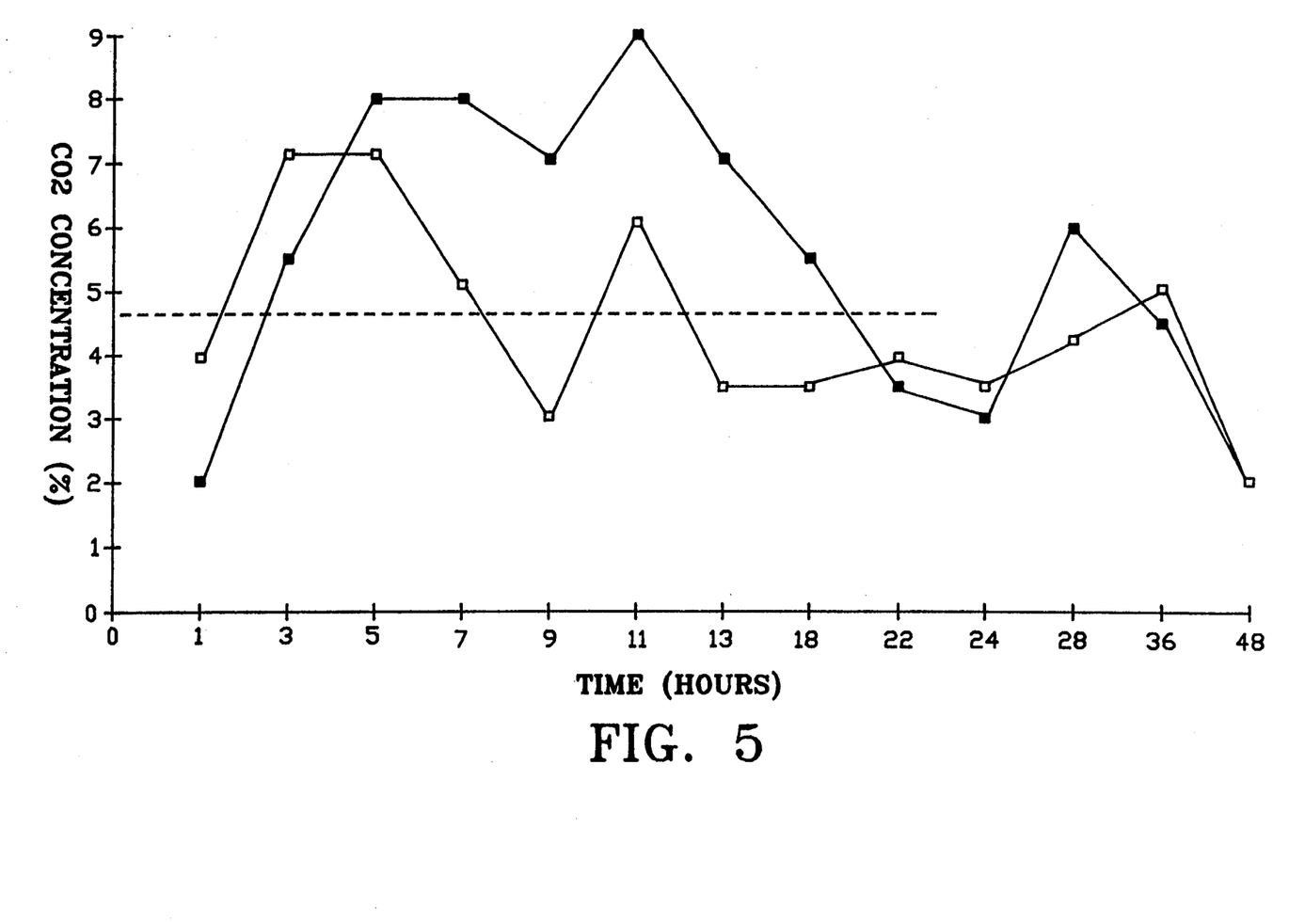
FIG. 5 illustrating carbon dioxide concentration at Hawaiian Flour Mills, Honolulu, Hi., with a filled square indicating measurements taken on a lower floor and a square outline indicating measurements taken on an upper floor.
Figure 6:
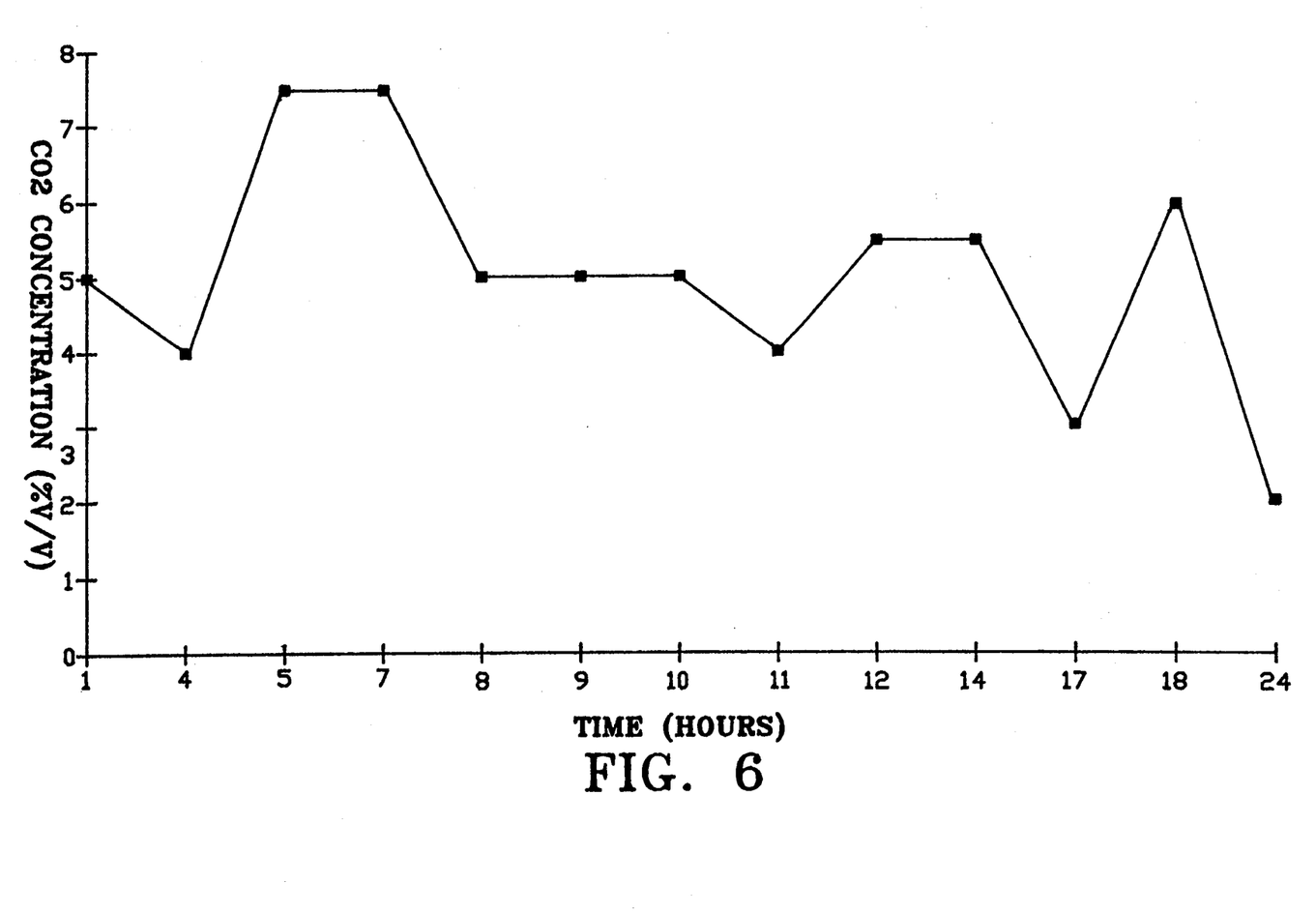
Figure 7:
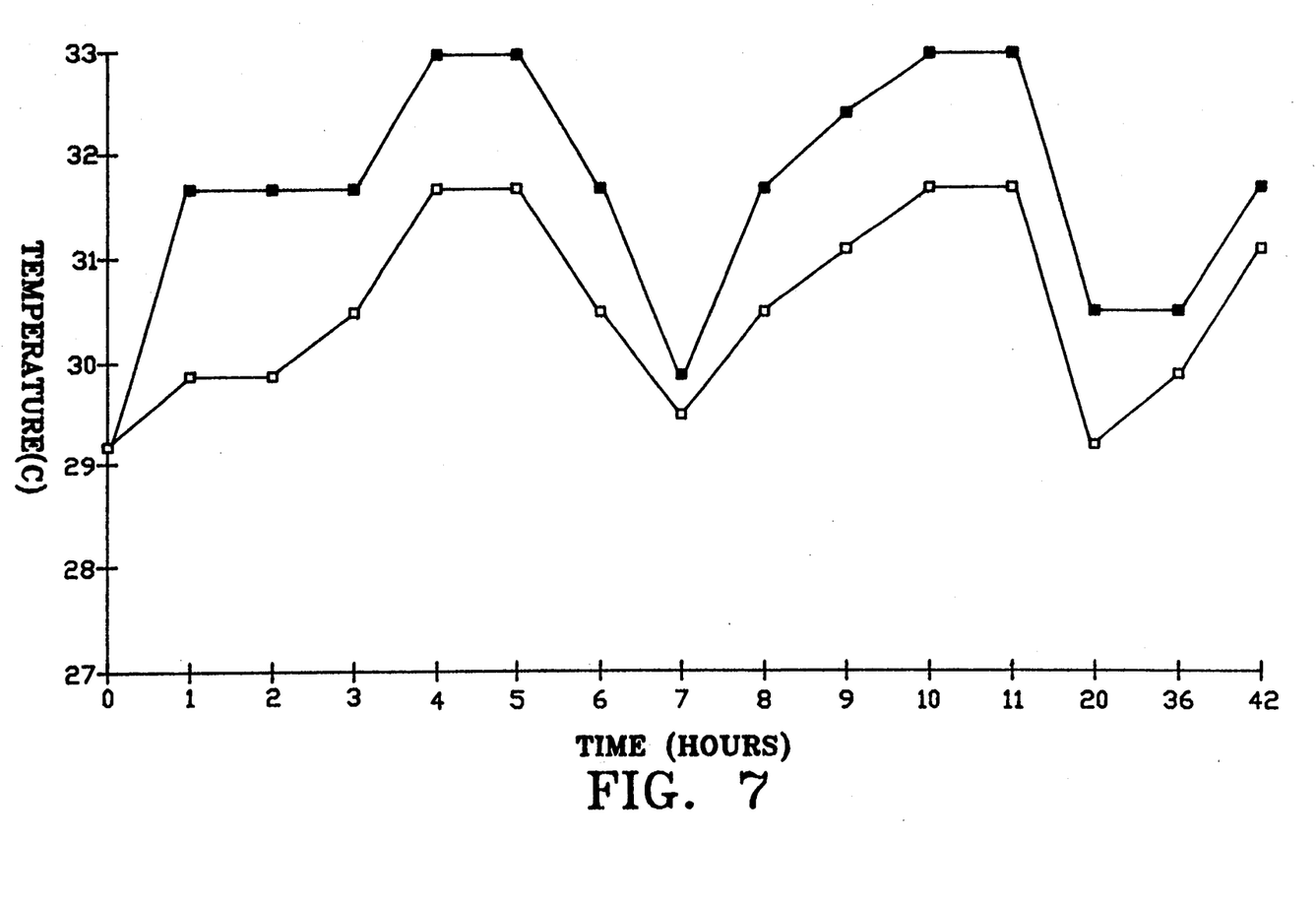
Figure 8:
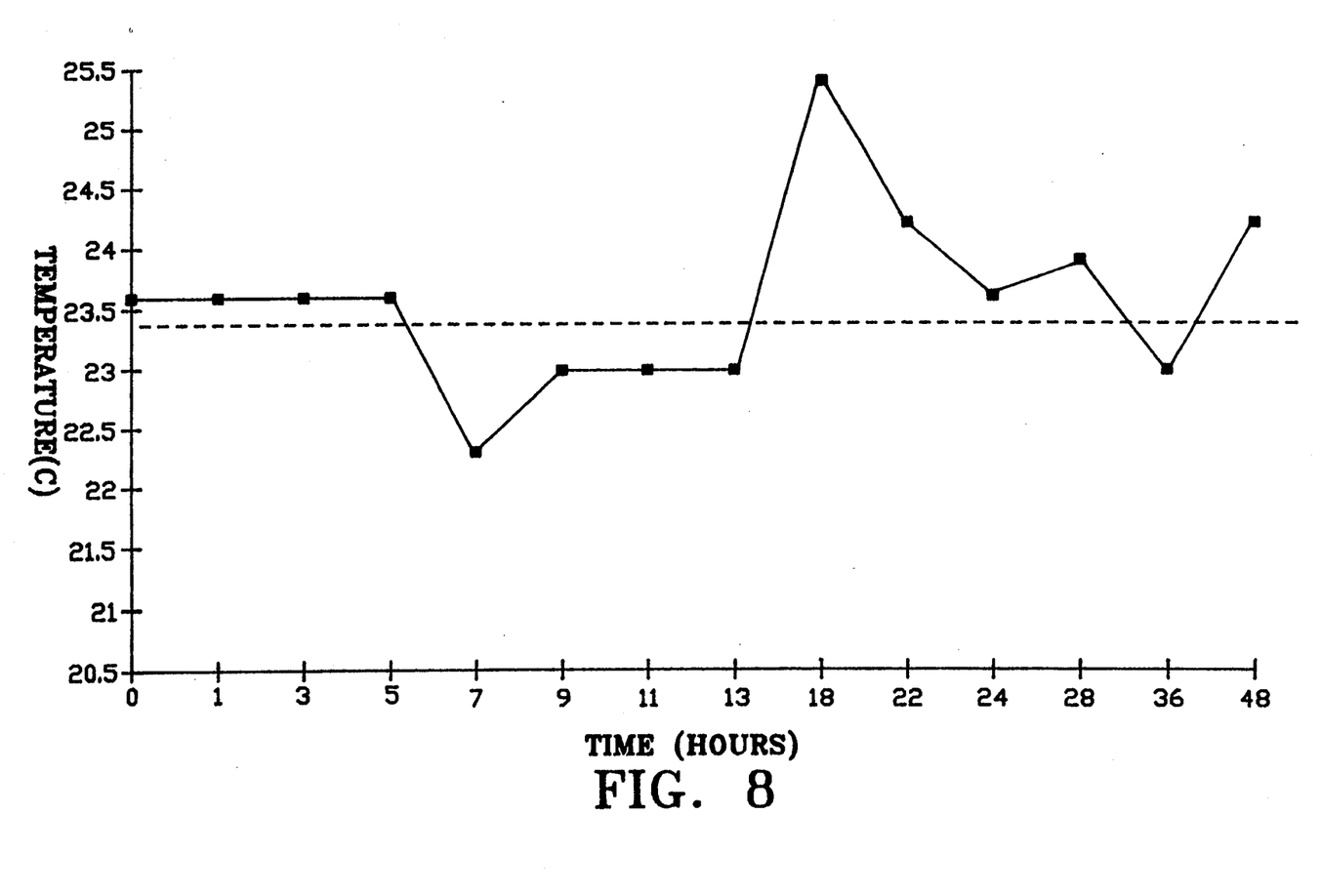
Figure 9:
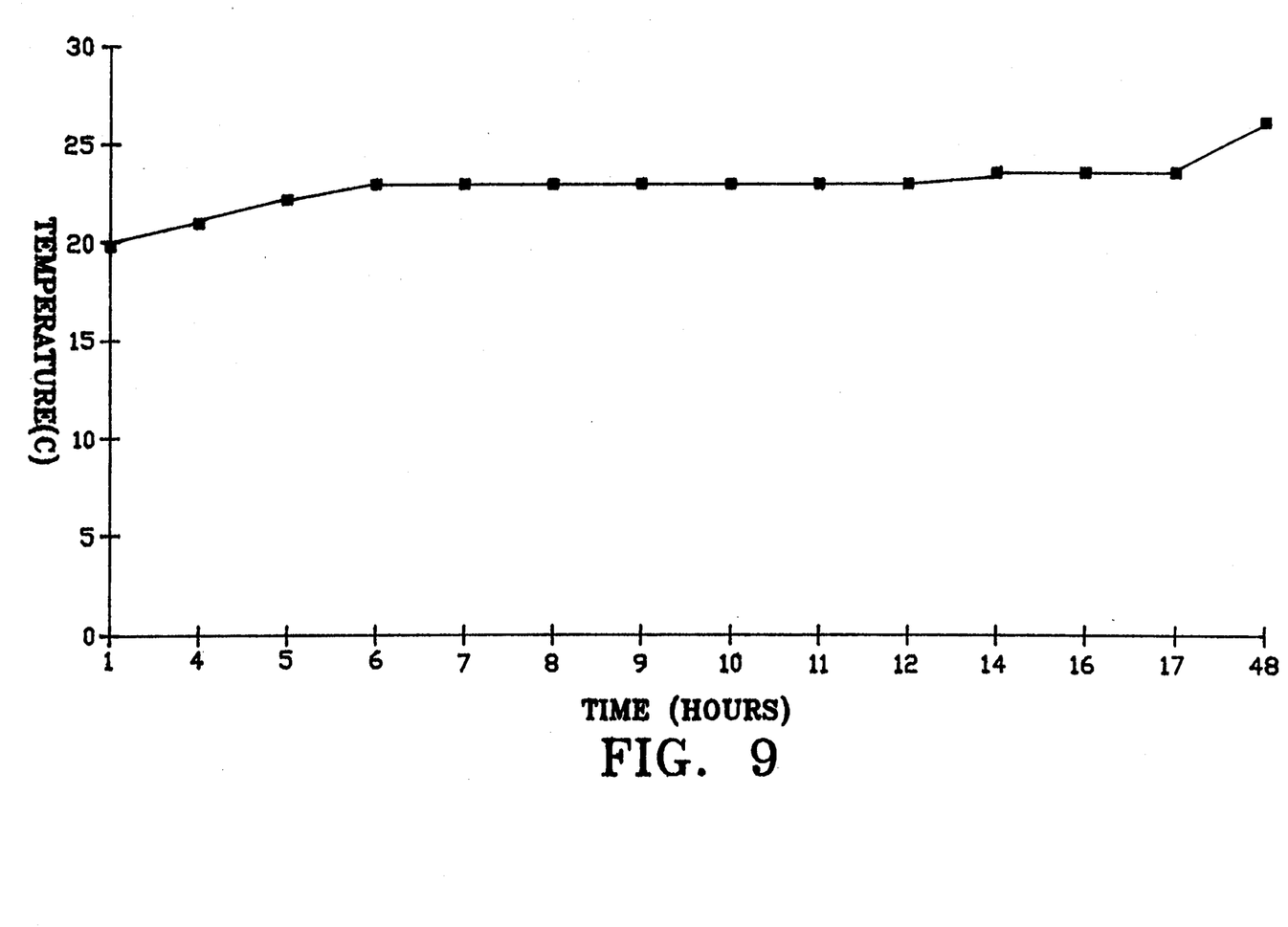

Fifty pound steel cylinders of liquid carbon dioxide were used as a source of carbon dioxide at Purdue Feed Mill. A total of 37 cylinders were used during the fumigation. The use of cylinders was cumbersome and more expensive than larger vessels used at the other two test sites. The carbon dioxide was vaporized from a liquid state to a gaseous state. The temperature of the carbon dioxide was raised to about 20-30 degrees Celsius prior to injection into the building. As those skilled in the art will appreciate, low temperature resistant hoses and regulators are needed when working with −40 degree Celsius liquid carbon dioxide. FIGS. 4 through 6 respectively illustrate carbon dioxide concentration as a function of time for the Purdue Feed Mill, the Hawaiian Flour Mill, and the Star of the West Mill.

The Purdue Feed Mill had electric heaters capable of maintaining an average 33 degree Celsius temperature within an error of about plus/minus 2 degrees Celsius. The Hawaiian Flour Mill was not artificially heated, maintaining a solar generated natural temperature of about 30-31 degrees Celsius. The Star of the West Mill required auxiliary heating to maintain a 32-37 degree Celsius temperature. A steam boiler was used to heat the radiators in the building and an additional steam coil-type 125,000 BTU heater was used to boost the heat capacity. The outdoor temperatures during the Michigan fumigation reached 4 degrees Celsius. The other two fumigations were warm summer days.

Test insects were placed in four locations at the Purdue Feed Mill. Four species of insects were utilized. This included the Angoumois grain moth (*Sitotroga cerealella*), Red flour beetles (*Tribolium castaneum*), Warehouse beetle (*Trogoderma variabile*), and Rice weevil (*Sitophilus oryzae*). The eggs, larvae, pupae, and adults were placed in 250 ml plastic containers. Two groups of 36 containers were placed on the first floor and two groups of 36 containers were placed on the second floor. Test insects were pulled from the fumigated mill starting at 20 hours from the start of the fumigation. Insects were then collected every four hours until 48 hours were completed. The adults and larval stages were observed and all insects were dead starting at 20 hours into the fumigation. All of the containers were taken back for laboratory analysis at Purdue University and incubated for 30 days in a growth chamber. After 30 days no insect activity was observed. The controls remained alive.

At the Hawaiian Flour Mill two species of stored-product insects were placed as bio-assays, including Red flour beetles (*Tribolium castanium*) eggs, larvae, pupae, and adults, with both Indiana strain and Hawaii strain utilized, and Rice weevil (*Sitophilus oryzae*) adults. A total of 150 insect cages with at least ten insects per cage were placed in the six floors. Insect cages were placed approximately one meter off the floor. Insect cages were pulled from the building starting at 13 hours from the start of the fumigation. The sample of insects pulled at 13 hours were dead in the bio-assays. All insects that were pulled from the flour mill at 24 hours after the beginning of the fumigation were dead. These insects were incubated in Hawaii and Indianapolis for 30 days with no activity observed. All indoor and outdoor controls were alive after 48 hours and 87% were alive after 30 days.

At Star of the West flour mill three species of stored-product insects were used for bio-assays, including Red flour beetle adults, larvae, pupae, and adults, Rice weevil adults, and Indianmeal moth eggs (*Plodia interpunctella*). Insect cages were placed on each floor and controls were maintained. Over 150 cages were placed in the mill with at least 10 insects per cage. Insect cages where pulled from the building after twelve hours. All adult and larvae specimens were dead after twelve hours from the beginning of the fumigation. All insect cages pulled from twelve hours to 24 hours were subsequently dead. All specimens were held at room temperature. No insect activity was observed in any of the stages of the three stored-product insects tested. Controls from outdoor cages and indoor cages remained alive.

To test penetrability of phosphine and carbon dioxide, twelve six inch diameter PVC pipes were capped and permanently sealed on one end. Insect cages were placed in the bottom of these six feet long tubes. Each tube was filled with wheat flour and insect cages were placed at a three foot level. Flour was added to the remaining three feet to fill the tubes completely. A 1.4 millimeter polyethylene bag was secured over the open end of the tube with tape. Two tubes were placed on each of the six floors of the Hawaiian Flour Mill. The first tube, from the first floor, was pulled from the fumigated building after thirteen hours from the beginning of the fumigation. All of the test insects were moving. The test insects were observed to be sluggish as compared to a control group. Five flour-filled tubes were pulled from the fumigated flour mill after 24 hours. Carbon dioxide and phosphine were detected with a Draeger tube at levels equal to the ambient of the fumigated mill. The phosphine levels under the polyethylene bag were 50 ppm and the carbon dioxide levels were 3%. The test insects at 3 feet and 6 feet were observed. The adults and larvae were dead. The eggs and pupae were incubated for 30 days with no emergence or activity. The remaining six tubes were pulled at 48 hours with the same results. In order to effect a kill on those test insects, the gases had to penetrate the 1.4 mil polyethylene bag, go through 3 to 6 feet of flour and inside a polyethylene bio-assay tube and kill eggs, larvae, pupae, and adult specimen insects. The control group was alive. After 30 days, the insects in the polyethylene vials on the bottom of the 6 foot flour tubes showed some activity.

A penetrability study was also conducted at Star of the West Mill, with two 5 foot and one 10 foot tube being placed in the fumigated mill. Insects were placed at 10 foot, 5 foot, and 1 foot levels in the tubes. A 1.4 millimeter polyethylene bag was placed over one five foot tube and no bags over the remaining five feet tube and the ten feet tube. After twelve hours the insects at the bottom of the five feet tube without a plastic bag were dead. After 24 hours the test insects at the bottom of the 5 feet tube with the bag and the ten feet tube were dead. The immature stages are being incubated at this time. These results indicate that the combination of phosphine, carbon dioxide, and elevated temperature provides a superior fumigating composition and method having high penetrability and effective pesticidal properties in a limited time.

While the present invention has been described in connection with specific embodiments, it will be apparent to those skilled in the art that various changes may be made therein without departing from the spirit or scope of the invention.

The invention claimed is:

1. A method for fumigating an enclosed building structure to control pests in said structure, comprising the steps of
    releasing sufficient phosphine into the enclosed building structure to maintain an average concentration of between about 50 and 200 ppm phosphine,
    concurrently releasing sufficient carbon dioxide into the enclosed building structure to maintain an average concentration of between about 4% and 20% carbon dioxide, and
    maintaining and/or raising the temperature in the enclosed building structure to between about 30 degrees Celsius and 40 degrees Celsius,
    wherein the steps of releasing phosphine, releasing carbon dioxide, and maintaining and/or raising the temperature of the enclosed structure is continued for a limited time not exceeding 72 hours.

2. The method of claim 1, wherein phosphine is maintained at an average concentration of between about 50 ppm and 200 ppm phosphine, carbon dioxide is maintained at an average concentration of between about 4% and 10% carbon dioxide, and the temperature is maintained at between about 30 degrees Celsius and 40 degrees Celsius.

3. The method of claim 1, wherein the step of releasing phosphine into the enclosed building structure further comprises hydrolysis of magnesium phosphide.

4. The method of claim 1, wherein the limited time is between about 12 hours to about 48 hours.

* * * * *